United States Patent
Spahn

(10) Patent No.: US 7,415,097 B2
(45) Date of Patent: Aug. 19, 2008

(54) METHOD FOR RECORDING CORRECTION FRAMES FOR HIGH ENERGY IMAGES

(75) Inventor: Martin Spahn, Chicago, IL (US)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/651,377

(22) Filed: Jan. 9, 2007

(65) Prior Publication Data

US 2007/0165617 A1    Jul. 19, 2007

(30) Foreign Application Priority Data

Jan. 13, 2006   (DE) .................. 10 2006 001 851

(51) Int. Cl.
*H05G 1/64*   (2006.01)

(52) U.S. Cl. ........................................ 378/98.8; 378/91

(58) Field of Classification Search ............... 378/91, 378/98, 98.8, 207, 210; 250/370.09, 370.11
See application file for complete search history.

(56) References Cited

FOREIGN PATENT DOCUMENTS

| DE | 103 24 590 A1 | 2/2004 |
|---|---|---|
| DE | 103 35 321 A1 | 3/2005 |

*Primary Examiner*—Jurie Yun

(57) ABSTRACT

It is proposed according to the invention to record, in an image recording device for recording X-ray images, offset frames for different operating modes of said device according to a current sequence, wherein said current sequence can, by taking into account a new sequence in a comparison procedure, be changed into an updated sequence. The new sequence is based on the frequency with which the individual operating modes are used.

20 Claims, 2 Drawing Sheets

METHOD FOR RECORDING CORRECTION FRAMES FOR HIGH ENERGY IMAGES

CROSS REFERENCE TO RELATED APPLICATIONS

This application claims priority of German application No. 10 2006 001 851.6 filed Jan. 13, 2006, which is incorporated by reference herein in its entirety

FIELD OF THE INVENTION

The invention relates to a method for recording correction frames for high energy images that are recorded in different operating modes of a device for recording high energy images.

BACKGROUND OF THE INVENTION

Methods of this kind are generally known. Correction frames need to be recorded in particular when using digital solid state detectors for X-ray imaging, since uncorrected X-ray images cannot be used for diagnostic purposes. It is only after X-ray images have been corrected with the aid of such correction frames that said X-ray images can realistically be post-processed using organ-specific image processing software and can then be diagnostically interpreted.

The necessity for correction frames arises from the physical characteristics of the solid state detectors used for X-ray imaging. In the case of said solid state detectors the optical and electrical properties of the individual pixels can show marked variations. For instance the leakage currents of the photodiodes and the switching transistors used for readouts can vary. Furthermore resistors and capacitors used for readouts can vary row by row and column by column. Also the amplifiers used for readouts can be embodied in different designs. Moreover the solid state detectors are occasionally made up from different sub-matrixes that exhibit different properties. These and other circumstances are the reason why among other things what is referred to as the offset varies widely across solid state detectors.

Furthermore the offset of the individual pixels is not constant, but varies over time. These variations can be provoked by temperature fluctuations, such as temperature changes in the sub-matrixes or temperature fluctuations in the electronic modules, or can also be dependent on the operating modes in which the solid state detector is operated. For example the offset can depend on the frame frequency, which in the case of fluoroscopy typically varies between three and sixty images per second. In other applications, images with X-ray windows of up to 2.5 seconds are recorded every half to three seconds. This is the case for instance with blurred image tomography. The offset can however also depend on the radiation dose, the readout mode, the readout range used and the radiation period.

Due in particular to the strong dependency on temperature, offset frames need to be created contemporaneously in relation to the X-ray plates being recorded in different operating modes or sequences. This is particularly true in the case of uncooled solid state detectors, since the variations in their temperature depend on the ambient temperature and the operating mode of the solid state detector concerned.

Furthermore devices for recording high energy images support a considerable number of operating modes. X-ray equipment for vascular angiography or cardiology can typically be operated in 30 to 40 different operating modes. Frequently it is not enough to take only one offset frame for all the various operating modes. Instead, up to 60 offset frames are recorded in order to suppress noise as far as possible. In the operational pauses between acquisitions of X-ray images of an object under investigation there is often not enough time available to create offset frames for all operating modes.

SUMMARY OF THE INVENTION

Based on this prior art, the object of the invention is to create a method for recording correction frames for high energy images that enables correction frames to be recorded contemporaneously in relation to the associated high energy images.

This object is achieved by means of a method with the features which will emerge from the independent claim. Advantageous embodiments and developments are specified in the dependent claims.

According to the method, the correction frames are recorded in a sequence determined by the frequency distribution of the operating modes. By this means preference is given to recording correction frames for the frequently used operating modes. On the other hand correction frames for operating modes that are rarely used are recorded at a greater distance in time. Since correction frames are created as a matter of priority for the frequently used operating modes, a contemporaneously recorded correction frame is available in most cases. The demand-led recording of the correction frames means that the available time is used effectively and in particular no correction frames are recorded for operating modes that are seldom if ever used.

In a preferred embodiment, the correction frames in a given time slot are recorded in a sequence corresponding to the frequency distribution of the operating modes in a preceding time slot. This approach enables the sequence in which the correction frames are recorded to be appropriately adapted to demand.

In a further preferred embodiment, the correction frames in a given time slot are recorded in a sequence corresponding to an overall frequency distribution obtained by averaging the frequency distributions in preceding time slots. In this embodiment an unusual series of operating modes does not immediately lead to a total change of sequence when recording the correction frames.

Immediately after starting up the device for recording high energy images, frequency distributions determined during the current live session are not available in every case for the operating modes in use. It is therefore possible in such cases to provide for the correction frames to be recorded in a predefined sequence. This sequence is preferably based on an expected frequency distribution for the individual operating modes.

The frequency distribution can be determined according to the time for which the device has been operated in a particular operating mode, or according to the number of recording operations carried out in a particular operating mode in a given time slot. Both procedures adequately determine the correction frame recording sequence.

BRIEF DESCRIPTION OF THE DRAWINGS

Further advantages and characteristics of the invention emerge from the description below, in which exemplary embodiments of the invention are explained in detail with reference to the accompanying drawings, in which.

DETAILED DESCRIPTION OF THE INVENTION

Figure 1:
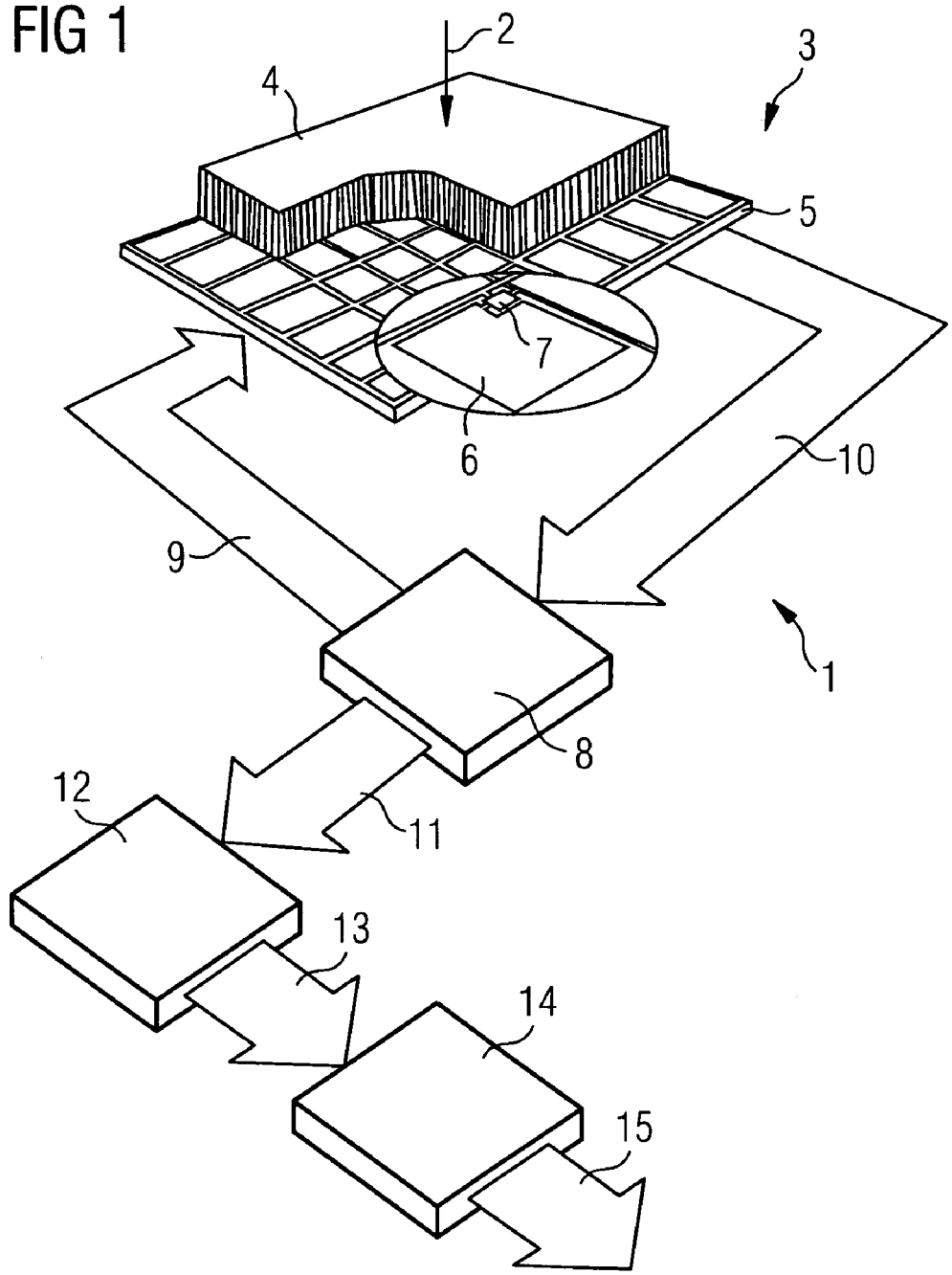
FIG. 1 shows a perspective view of an image recording device with a partially cut away flat frame detector with indirect conversion.

FIG. 1 shows an image recording device 1 which forms part of an X-ray machine that includes an X-ray source (not shown in FIG. 1) for generating X-rays 2. The X-rays 2 pass through an object requiring fluoroscopy and impinge on a flat frame detector 3. The flat frame detector 3 includes a scintillator 4. Beneath the scintillator 4 is an active matrix 5 which is usually manufactured from amorphous silicon. On the active matrix 5 an array of photodiodes 6 is formed. The light generated in the scintillator 4 over the respective photodiode 6 is absorbed in the photodiodes 6. During absorption electron-hole pairs are created, and in each case move to the anode and cathode of the respective photodiode 6. The charge quantity created by this means in the photodiode 6 is stored in the said photodiode 6 until said photodiode 6 is read out with the aid of an active switching element 7. For this the active switching elements 7 are activated row by row by a readout circuit 8 via address line 9. The charge stored in the photodiodes 6 is read out column by column via column lines 10. The read out charge is then converted from analog to digital in the analyzing circuit 8. This produces image data 11 which undergoes image preprocessing 12. The image preprocessing 12 produces preprocessed image data 13 which then undergoes organ-specific image processing 14. The organ-specific image processing 14 produces processed image data 15 which is suitable to be displayed on a display unit.

It should be mentioned that direct conversion flat frame detectors can also be used in place of indirect conversion flat frame detectors 3. Flat frame detectors with direct conversion of this kind have a converter that is made for example from selenium and immediately generates an electrical charge which is then stored on an electrode. Other flat frame detectors that can be used to create digital X-ray images are based on CCDs (charge coupled devices), APSs (active pixel sensors) or CMOS chips.

In the case of the flat frame detector 3 the physical characteristics of the pixels formed by the individual photodiodes 6 vary. Possible reasons for this may be the leakage currents of the photodiodes 6 or the active switching elements 7. Furthermore varying resistors and capacitors can contribute to the variation in the pixels from row to row or from column to column. In addition the variations from column to column in the inputs from the amplifiers used to read out the charges from the photodiodes 6 also lead to differences in the physical characteristics of the pixels. Moreover the flat frame detectors 3 can also be made up from a plurality of sub-matrixes. Large flat frame detectors 3 are typically built up from 1×2 or 2×2 sub-matrixes. These sub-matrixes in turn can differ with regard to their optical and electrical characteristics.

Similar variations can also occur in the case of the other types of flat frame detectors mentioned above.

Other things that are recorded include dark frames, also known as offset frames. Their purpose is to correct the various electrical and optical characteristics of the individual pixels. Sensitivity differences in the individual pixels of the flat frame detector 3, on the other hand, are captured by calibration frames. Offset frames and calibration frames enable the different electrical and optical characteristics of individual pixels in the flat frame detector 3 to be corrected. Even defective pixels in the flat frame detector 3 can be identified and corrected as necessary.

In particular the offset frames must be recorded as closely as possible in time to the actual acquisition frames in which the object under investigation is examined with X-rays. This is because the offset frames are subject to fluctuations caused by temperature differences and by the flat frame detector 3 being used in different operating modes. For example both the temperature of the sub-matrixes and the temperature of the electronic modules in the readout circuit 8 can vary. Furthermore the frequency with which frames are recorded with the aid of the flat frame detector 3 can fluctuate. Typically the frequency with which frames are recorded using the flat frame detector 3 is between three and sixty images per second. Additionally there is considerable variation in the detector dose received by the flat frame detector 3, depending on the application. The flat frame detector 3 receives a higher detector dose in fluoroscopy than in radiography. Also the individual or combined reading out of pixels, known as binning, influences the offset. For example with modern flat frame detectors 3, 1×1, 2×2 or 3×3 pixels can be read out simultaneously and combined in one binned pixel. The size of the readout range also plays a role. For example flat frame detectors may be read out either in their entirety or only in a zoom range. In conclusion a further factor is the duration of the exposure time.

The internal temperature of the flat frame detector 3 fluctuates considerably in particular in uncooled detectors. Offset images should therefore be recorded as near contemporaneously as possible. However, there is often not enough time available for recording offset frames. This is because the flat frame detectors 3 can be operated in as many as 40 different operating modes depending on the application, so that the time between acquisitions of X-ray images of an object under investigation is often not long enough to record offset frames for all operating modes.

Figure 2:
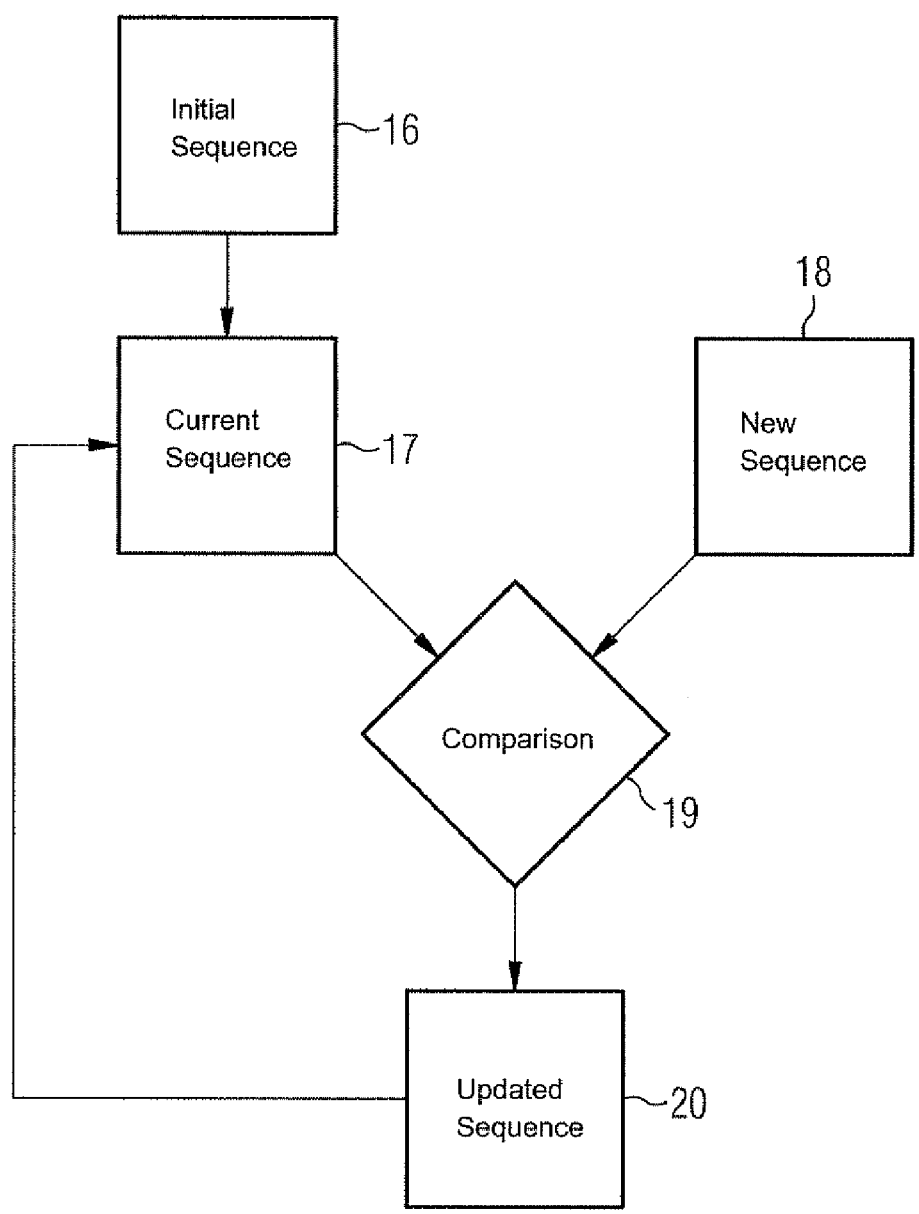
FIG. 2 is a flowchart showing the steps in the method for determining the sequence of offset frames.

According to the method shown in FIG. 2, a priority list by which offset frames will be recorded is created. For this purpose, in consecutive time slots the frequency of the different operating modes is determined and the priority list is updated according to the frequency of the individual operating modes. On the priority list the offset frames that are to be recorded in the different operating modes are sorted into a sequence corresponding to the frequency of the different operating modes. Frequently used operating modes are sorted to the early part of the sequence, whereas seldom if ever used operating modes are sorted to the end of the sequence. Then during the acquisition mode of the image recording device 1 the priority list is processed from start to finish in the sequence listed in said priority list by first creating offset frames for the operating mode at the beginning of the sequence, and then recording offset frames for the further operating modes provided there is enough time available between acquisitions of X-ray images. Operating modes for which no offset frames could be created between acquisitions of X-ray images then receive updated offset frames after the end of the acquisition mode if necessary.

If no frequency distribution has been determined in the current mode, the method starts with an initial sequence 16 which is used as a current sequence 17 for the creation of the offset frames in a current time slot. The current sequence 17 corresponds to the frequency distribution of the operating modes in a preceding time slot. Furthermore in the current time slot a new sequence 18 is created, based on the frequency of the different operating modes in the current time slot. A comparison 19 is then made and used as the basis for creating an updated sequence 20.

Within the scope of the comparison 19, the updated sequence 20 can simply be made equal to the new sequence 18, or can be an updated sequence 20 created by weighting the frequencies.

This point will be explained below by means of a numerical example.

In this example the flat frame detector 3 can provide 30 operating modes. The flat frame detector 3 is subjected to X-rays 2 for a total of 30 minutes in a period of one hour. In the measurement period of 30 minutes during which the flat frame detector is in acquisition mode, it can be assumed that the following operating modes were used:
Operating mode 3: 5 minutes
Operating mode 7: 14 minutes
Operating mode 10: 1 minute
Operating mode 11: 10 minutes
Remaining operating modes: 0 minutes On occasions it is necessary to wait 5 or 10 minutes before starting to record offset frames, in order to be sure that there is actually an inactive phase. If the wait is 5 minutes, the total waiting time for four series of acquisitions can be 20 minutes, leaving only 10 minutes for recording offset frames. These 10 minutes are not enough time in every case to complete the recording of offset frames. Moreover, the 10 minutes are not available as a single period, but instead can be distributed throughout the whole hour, so it is an advantage if the most urgently needed offset frames are recorded first.

The frequency with which the operating modes are used gives rise to the following sequence for updating the offset frames: 7, 11, 3, 10 and then all the other operating modes. The other operating modes can be updated in their numerical sequence, for example.

After the 30-minute measurement period the current sequence 17 could be converted to the new sequence 18 determined above.

However, the updated sequence 20 can also be determined by weighted averaging of the frequency distributions in the current measurement period and a preceding measurement period. If for example the current sequence according to the frequency distribution in the preceding measurement period is 11, 7, 25, 3, 20 and then all the others, the current sequence 17 can be used as the basis and the new sequence 18 can be calculated using a weighting. In this way the updated sequence 20 would alter only slowly and the frequency distributions of preceding measurement periods would also be taken into account.

If for example the operating modes 11 and 7 occur in the preceding measurement period with the following frequency:
Operating mode 7: 6 minutes
Operating mode 11: 3 minutes the ranking of operating mode 7 and operating mode 11 in the updated list 20 would not change:
Operating mode 7: 6 min·70%+14 min·30%=8.4 min
Operating mode 11: 3 min·70%+10 min·30%=5.1 min The operating mode 7 would predominate in the weighted evaluation as before. Other operating modes situated further down in the current sequence 17 or the new sequence 18 may however change places.

In periods of inactivity when no X-ray images of the object under investigation are being acquired, offset frames are recorded for the latest operating modes to be dealt with in the current sequence 17.

The initial sequence 16, which is used when the image recording device 1 is newly installed or reset, could in this example be the numerical sequence 1 to 30 or be preset according to a frequency distribution that could reasonably be expected.

It should be noted that in the example mentioned above, the operating modes are sorted according to the length of time for which they are used in the time slots. It is however also conceivable to count the number of recordings in a given operating mode and then sort the sequence on the basis of the numbers captured. Rather than capturing the frequency in realtime slots, it is also conceivable to capture the frequency in operating time slots. In this case the only time slots taken into account are those in which the X-ray equipment is either switched on and ready to operate or in which the equipment is operating and acquiring X-ray images of an object under investigation.

Finally it should be noted that the method for creating offset frames described here can in principle also be used for further correction frames, for example for recording calibration frames.

The invention claimed is:

1. A method for recording a plurality of correction frames of a recording device, comprising:
   recording a plurality of acquisition frames in a plurality of operating modes by the recording device;
   determining a sequence based on a frequency distribution of the operating modes; and
   recording the correction frames by the recording device according to the sequence.

2. The method as claimed in claim 1, wherein the acquisition frames are corrected by the correction frames recorded in same operating modes.

3. The method as claimed in claim 1, wherein the sequence in a subsequent time slot is determined in accordance with the frequency distribution of the operating modes in a current time slot.

4. The method as claimed in claim 1, wherein the sequence in a subsequent time slot is determined by a weighted average of the frequency distribution of the operating modes in a current time slot and in a preceding time slot.

5. The method as claimed in claim 1, wherein the sequence is predefined if the frequency distribution of the operating modes is not available.

6. The method as claimed in claim 5, wherein the predefined sequence is determined according to an expected frequency distribution of the operating modes.

7. The method as claimed in claim 1, wherein the correction frames for unused operating modes are recorded in a predefined sequence.

8. The method as claimed in claim 7, wherein the predefined sequence is determined according to an expected frequency distribution of the operating modes.

9. The method as claimed in claim 1, wherein no correction frames are recorded for unused operating modes.

10. The method as claimed in claim 1, wherein the frequency distribution of the operating modes is determined according to a length of time for which the operating modes are used.

11. The method as claimed in claim 1, wherein the frequency distribution of the operating modes is determined according to a number of recording operations performed in the operating modes.

12. The method as claimed in claim 1, wherein the recording device is an X-ray image recording device used in a medical procedure.

13. A device for recording a plurality of acquisition frames of a patient in a medical procedure, comprising:
   a plurality of operating modes in which the acquisition frames are recorded;
   a computing unit that determines a sequence based on a frequency distribution of the operating modes; and
   a correcting unit that corrects the acquisition frames using correction frames recorded by the device in same operating modes, wherein the correction frames are recorded by the device according to the sequence.

14. The device as claimed in claim 13, wherein the sequence in a subsequent time slot is determined in accordance with the frequency distribution of the operating modes in a current time slot.

15. The device as claimed in claim 13, wherein the sequence in a subsequent time slot is determined by a weighted average of the frequency distribution of the operating modes in a current time slot and in a preceding time slot.

16. The device as claimed in claim 13, wherein the sequence is predefined if the frequency distribution of the operating modes is not available.

17. The device as claimed in claim 16, wherein the predefined sequence is determined according to an expected frequency distribution of the operating modes.

18. The device as claimed in claim 13, wherein the correction frames for unused operating modes are recorded in a predefined sequence.

19. The device as claimed in claim 18, wherein the predefined sequence is determined according to an expected frequency distribution of the operating modes.

20. The device as claimed in claim 13, wherein the frequency distribution of the operating modes is determined according to:

a length of time for which the operating modes are used, or a number of recording operations performed in the operating modes.

* * * * *